US007217507B2

(12) United States Patent
Hammond et al.

(10) Patent No.: US 7,217,507 B2
(45) Date of Patent: May 15, 2007

(54) METHOD FOR DETECTING LIGANDS AND TARGETS IN A MIXTURE

(75) Inventors: David J. Hammond, Laytonsville, MD (US); Julia Tait Lathrop, Falls Church, VA (US)

(73) Assignee: The American National Red Cross, Falls Church, VA (US)

( * ) Notice: Subject to any disclaimer, the term of this patent is extended or adjusted under 35 U.S.C. 154(b) by 455 days.

(21) Appl. No.: 10/414,523

(22) Filed: Apr. 14, 2003

(65) Prior Publication Data
US 2003/0211471 A1 Nov. 13, 2003

Related U.S. Application Data

(60) Provisional application No. 60/372,091, filed on Apr. 15, 2002.

(51) Int. Cl.
C12Q 1/70 (2006.01)
C12Q 1/68 (2006.01)
C12Q 1/46 (2006.01)
(52) U.S. Cl. .................. 435/5; 435/6; 435/20
(58) Field of Classification Search ............ 435/5, 435/6, 7.2, 7.31, 7.32, 7.93, 20
See application file for complete search history.

(56) References Cited

U.S. PATENT DOCUMENTS

| 5,010,175 | A |   | 4/1991  | Rutter et al.              |
|-----------|---|---|---------|----------------------------|
| 5,133,866 | A | * | 7/1992  | Kauvar ............. 210/635 |
| 5,235,039 | A |   | 8/1993  | Heath, Jr. et al.          |
| 5,498,538 | A |   | 3/1996  | Kay et al.                 |
| 5,601,992 | A |   | 2/1997  | Lerner et al.              |
| 5,639,603 | A |   | 6/1997  | Dower et al.               |
| 5,834,318 | A | * | 11/1998 | Buettner ............ 436/518 |
| 5,840,485 | A |   | 11/1998 | Lebl et al.                |
| 5,856,083 | A |   | 1/1999  | Chelsky et al.             |
| 5,981,254 | A | * | 11/1999 | Bui-Khac ............ 435/214 |
| 6,090,912 | A |   | 7/2000  | Lebl et al.                |
| 6,783,969 | B1| * | 8/2004  | Tang et al. ........... 435/219 |
| 6,815,535 | B1| * | 11/2004 | Kanellos et al. ...... 530/412 |
| 6,905,688 | B2| * | 6/2005  | Rosen et al. ........ 424/192.1 |
| 7,041,790 | B2| * | 5/2006  | Wescott et al. ....... 530/328 |
| 2003/0232054 | A1| * | 12/2003 | Tang et al. .......... 424/185.1 |

FOREIGN PATENT DOCUMENTS

| EP | 0742438 A  |   | 11/1996 |
|----|------------|---|---------|
| WO | WO-92/00091 | * | 1/1992 |
| WO | WO 92/00091 A |   | 1/1992 |
| WO | WO 97/01098 A |   | 1/1997 |
| WO | WO 01/31019 A2 |   | 5/2001 |
| WO | WO 01/40265 A |   | 6/2001 |
| WO | WO 03/016904 A2 |   | 2/2003 |

OTHER PUBLICATIONS

Phizicky, E.M. et al. Protein—Protein Interactions: Methods for Detection and Anlaysis. 1995.Microbiological Reviews, vol. 59, pp. 94-123.*
Turck, C. W. Excerpt from Peptide Research, 1994, pp. 396-400.*
Buettner et al., "Chemically Derived Peptide Libraries: A New Resin and Methodology for Lead Identification," *Int. J. of Peptide & Protein Res.*, vol. 47, 70-83 1996).
Devlin et al., "Random Peptide Libraries: A Source of Specific Protein-Binding Molecules," *Science*, vol. 249, 404-406 (1990).
Hammond, "Identification of Affinity Ligands from Peptide Libraries and their Applications," *Chromatographia*, vol. 46, No. 7/8, 475-476 (1998).
Lam et al., "A New Type of Synthetic Peptide Library for Identifying Ligand-binding Activity," *Nature*, vol. 354, No. 6348, 82-84 (1991).
Still, "Discovery of Sequence-Selective Peptide Binding By Synthetic Receptors Using Encoded Combinatorial Libraries," *Acc. Chem. Res.*, vol. 29, 155-163 (1996).
Baumbach et al., "Protein Purification Using Affinity Ligands Deduced from Peptide Libraries," *BioPharm.*, May 24-31 (1992).
Furka et al., "General Method for Rapid Synthesis of Multicomponent Peptide Mixtures," *Int. J. Peptide Protein Res.*, 37: 487-493 (1991).
Hackeng et al., "Low-density Lipoprotein Enhances Platelet Secretion Via Integrin-alpha$_{IIb}$beta$_3$-Mediated Signaling," *Arteriosclerosis Thromb. Vasc. Biol.*, 19(2): 239-247 (1999).
Katz et al., "Surface Reconstitution of a de novo Synthesized Hemoprotein for Bioelectronic Applications," *Angew. Chem. Int. Ed.*, 37(23): 3253-3256 (1998).
Racusen et al., "Microscale, Filtration-Type Binding Assay for Studying Myosin-Erythrocyte Protein 4.1 Interactions," *Analytical Biochemistry*, 188: 344-348 (1990).
Sugg et al., "Cyclic Lactam Analogues of Ac-[Nle$^4$]alpha-MSH$_{4-11}$-NH$_2$," *Biochemistry*, 27(21): 8181-8188 (1988).
Turck, "Radioactive Screening of Synthetic Peptide Libraries," *Companion to Methods in Enzymology*, 6(4): 396-400 (1994).

(Continued)

*Primary Examiner*—Jon Weber
*Assistant Examiner*—Kailash C. Srivastava
(74) *Attorney, Agent, or Firm*—Merchant & Gould, P.C.; Suzanne E. Ziska

(57) ABSTRACT

The invention provides a method of characterizing a target that binds to a ligand. The method comprises providing ligands, optionally attached to a support, and contacting the ligands with targets to allow at least one target to bind to at least one ligand. The method further comprises immobilizing the resulting complexes in a first matrix, such that each complex has a different position within the first matrix, and transferring the target of the complex to a second matrix. The position of the target within the second matrix corresponds to the position of the ligand-support complex within the first matrix. The target on the second matrix is then detected.

14 Claims, No Drawings

OTHER PUBLICATIONS

Patrick G. Swann et al., "Nonspecific Protease-Catalyzed Hydrolysis/Synthesis of a Mixture of Peptides: Product Diversity & Ligand Amplification by a Molecular Trap", BIOPOLYMERS, vol. 40, No. 6, pp. 617-625 (1996).

C. Kuyas et al., "Isolation of Human Fibrinogen and its Derivatives by Affinity Chromatography on Gly-Pro-Ang-Pro-Lys-Fractogel", Thrombosis & Haemostasis, 63 (3), 1990, pp. 439-444.

Deborah B. Kaufman et al., "Affinity Purification of Fibrinogen Using a Ligand from a Peptide Library", Biotechnology & Bioengineering, vol. 77, No. 3, pp. 278-289, Feb. 5, 2002.

K. Mondorf et al., "Screening of combinational peptide libraries: Identification of ligands for affinity purification of proteins using a radiological approach", J. Peptide Res. 52, 1998, pp. 526-536.

Jean Cohen et al., "Cloning of Bovine Rotavirus (RF Strain): Nucleotide Sequence of the Gene Coding for the Major Capsid Protein", VIROLOGY 138, 178-182 (1984).

E. Kohli et al., "Epitope Mapping of the Major Inner Capsid Protein of Group A Rotavirus Using Peptide Synthesis", Virology, 194, 110-116 (1993).

\* cited by examiner

METHOD FOR DETECTING LIGANDS AND TARGETS IN A MIXTURE

CROSS-REFERENCE TO RELATED PATENT APPLICATIONS

This patent application claims the benefit of U.S. Provisional Patent Application No. 60/372,091, filed Apr. 15, 2002.

FIELD OF THE INVENTION

The present invention pertains to methods of characterizing a target that binds to a ligand.

BACKGROUND OF THE INVENTION

Affinity chromatography is a common method for concentrating and separating target molecules from a sample, and is based on specific, three-dimensional interactions between target molecules and entities to which they bind (i.e., ligands). Ligands can be isolated or generated for binding to practically any target molecule. Potential ligands include biological molecules such as proteins, antibodies, peptides, and the like. Libraries of millions of potential ligands are generated using combinatorial synthesis techniques, many of which are well known in the art (see, for example, Lam et al., *Nature*, 354, 82–84 (1991) and International Patent Application WO 92/00091). To aid in separation of target molecules from a sample, ligands can be affixed to a solid support matrix, such as individual particles (e.g., chromatography resin beads) or contiguous supports (e.g., arrays). Ligands immobilized on a solid support matrix can then be employed to purify targets from complex solutions (Baumbach and Hammond, *BioPharm May*, 24–31 (1992)).

Aside from mere separation of target molecules from a sample, affinity chromatography provides a means of examining binding interactions between potential ligands and target molecules. Detecting target-ligand binding can be challenging. Techniques for detecting ligand-target complexes have been developed, e.g. radiolabelling and immunological methods (see, for example, U.S. Pat. No. 5,834,318, International Patent Application WO 01/40265, and U.S. patent application Ser. No. 09/453,115). However, currently available detection techniques have potential drawbacks, namely modification of the target through radiolabel attachment, interference from ligand-target-detection system interactions, and the ability to detect only a limited number of targets for which detection systems already exist.

In view of the above, there remains a need in the art for a method of detecting target-ligand binding that avoids modification of the target for detection, enables detection of a target separated from a ligand and identification of the ligand, and allows detection of the target via its biological, biochemical or chemical activity. The invention provides such a method. These and other advantages of the invention, as well as additional inventive features, will be apparent from the description of the invention provided herein.

BRIEF SUMMARY OF THE INVENTION

The invention provides a method of characterizing a target that binds to a ligand. In one embodiment, the method comprises (i) providing one or more ligands, wherein each ligand is attached to a support to form one or more ligand-support complexes, (ii) contacting the ligand-support complexes with one or more targets under conditions that allow at least one target to bind to at least one ligand-support complex, thereby forming one or more target-ligand-support complexes, (iii) immobilizing the ligand-support complexes and the target-ligand-support complexes in a first matrix, such that each ligand-support complex and each target-ligand-support complex has a different position within the first matrix, (iv) transferring at least some of the target of at least one target-ligand-support complex to a second matrix so that the ligand-support complex of the target-ligand-support complex remains in the first matrix, wherein the position of the target within the second matrix corresponds to the position of the ligand-support complex within the first matrix, and (v) detecting the target on the second matrix.

Alternatively, the method of characterizing a target that binds to a ligand comprises (i) providing one or more ligands, (ii) immobilizing each of the ligands to a first matrix, such that each of the ligands has a different position within the first matrix, (iii) contacting the ligands within the first matrix with one or more targets under conditions that allow at least one target to bind to at least one ligand, thereby forming one or more target-ligand complexes within the first matrix, (iv) transferring at least some of the target of at least one target-ligand complex within the first matrix to a second matrix so that the ligand of the target-ligand complex remains in the first matrix, wherein the position of the target within the second matrix corresponds to the position of the ligand within the first matrix, (v) detecting the target on the second matrix. These methods allow for the characterization of a target that binds to a ligand.

DETAILED DESCRIPTION OF THE INVENTION

The invention provides a methodology to detect simultaneously a target molecule, following its separation from a sample, and, optionally, to provide identification of a ligand that binds specifically to the target. In particular, the invention provides a method of characterizing a target that binds to a ligand. The method comprises (i) providing one or more ligands, wherein each ligand is attached to a support to form one or more ligand-support complexes, (ii) contacting the ligand-support complexes with one or more targets under conditions that allow at least one target to bind to at least one ligand-support complex, thereby forming one or more target-ligand-support complexes, (iii) immobilizing the ligand-support complexes and the target-ligand-support complexes in a first matrix, such that each ligand-support complex and each target-ligand-support complex has a different position within the first matrix, (iv) transferring at least a portion of the target (i.e., one or more target molecules) of at least one target-ligand-support complex to a second matrix so that the ligand-support complex of the target-ligand-support complex remains in the first matrix, wherein the position of the target within the second matrix corresponds to the position of the ligand-support complex within the first matrix, and (v) detecting the target on the second matrix. Alternatively, the method comprises (i) providing one or more ligands, (ii) immobilizing each of the ligands to a first matrix, such that each of the ligands has a different position within the first matrix, (iii) contacting the ligands within the first matrix with one or more targets under conditions that allow at least one target to bind to at least one ligand, thereby forming one or more target-ligand complexes within the first matrix, (iv) transferring at least a portion of the target of at least one target-ligand complex within the first matrix to a second matrix so that the ligand of the target-ligand complex remains in the first matrix, wherein the position of the target within the second matrix corresponds to the position of the ligand within the first matrix, (v) detecting the target on the second matrix. The inventive method, thus, allows characterization of a target that binds to a ligand.

The invention offers a number of advantages over previous ligand and target screening methods. First, a target and its cognate ligand can be detected after dissociation. Additionally, both the target and its ligand are detected without the necessity for prior modification. Thus, interaction between the components of the detection system and the ligand, supports, or other elements of the system is avoided. Second, because all of the components within a sample can be captured in unique positions on the first and second matrices, the second matrix can be screened sequentially or simultaneously for the presence of multiple, independent targets. Yet another advantage of the invention is that the biological, biochemical, and chemical activity of the target can be maintained, if desired. Transfer conditions can be advantageously controlled to transfer a subpopulation of the bound target at any one time, to identify specific elution conditions of targets, or to selectively transfer target isotypes. Indeed, by varying elution conditions, it is possible to distinguish between molecular or biological entities that are substantially identical in chemical or primary structure or enantiomers and, therefore, exhibit different three-dimensional or tertiary structure. Moreover, it is also possible to identify ligands that specifically bind to active sites on a target molecule by transferring the target to a second matrix using transfer buffer containing molecules that compete for binding to the active site. These properties confer important advantages to the inventive method over technology described in the prior art.

Target

For purposes of the present invention, the term "target" as used herein refers to any biological, chemical, or biochemical entity, such as a compound, molecule, virus, or cell, that binds to a ligand. The target can be isolated from nature or synthetically produced, and can be organic or inorganic in nature (e.g., a synthetic inorganic compound or a synthetic organic compound). For example, the target can be a drug or drug candidate (such as a small molecule drug candidate), a fertilizer component, an insecticide component, or a derivative, analogue, or enantiomer thereof. In addition, the target can be endogenous or exogenous to any prokaryote or eukaryote, e.g., a bacterium, a fungus, yeast, a plant, or a mammal. Suitable targets for the inventive method include, but are not limited to, cells (e.g., stem cells or cells in culture), bacteria, viruses, yeast, proteins, peptides, protein complexes (e.g., blood clotting Factor XIII and fibrinogen or blood clotting Factor VIII and Von Willebrand Factor), prions, amino acids, nucleic acids, carbohydrates, lipids, isoforms of any of the foregoing, and combinations of any of the foregoing. Preferably, the targets are proteins. Suitable protein targets include, for example, receptors, antibodies, immunogens, enzymes (e.g., proteases), and enzyme substrates. More preferably, the proteins are plasma proteins. Plasma proteins include, for example, butyrylcholinesterase (BChE), fibrinogen, $\alpha$-1 proteinase inhibitor, apolipoprotein A1 (also known as Apo-A1 lipoprotein), immunoglobulins, paraoxonase, or coagulation factors, all of which are naturally found in the plasma of an organism in a non-diseased state. Alternatively, the plasma protein is present in plasma associated with a diseased state (optionally not found in the plasma of a healthy subject) or as a result of the administration of an agent, e.g., a drug. In this regard, the plasma protein can be an infectious PrPsc prion protein.

The target of the inventive method can be obtained from any source. A sample comprising the target can be a complex solution, such as extracts of soil, air, water, food, swabs for evaluating environmental contamination, intermediate or end-stage chemical reaction mixtures, and the like. The sample comprising the target can be a chemical or synthetic mixture and can be present in a combinatorial library and/or present in organic solvents under extreme conditions of pressure, temperature, etc. Preferably, the targets are present in or isolated from a biological fluid. By "biological fluid" is meant any aqueous solution that is derived from a prokaryotic or eukaryotic organism. The biological fluid can be obtained directly from the prokaryotic or eukaryotic organism, such as blood, lymph, tears, saliva, perspiration, and urine. Alternatively, the biological fluid can be obtained by culturing cells of the organism, such as fermentation broth and cell culture medium. Suitable biological fluids for use in the inventive method includes, but are not limited to, blood, plasma, serum, a cell homogenate, a tissue homogenate, a conditioned medium, a fermentation broth, cerebrospinal fluid, urine, saliva, milk, ductal fluid, tears, perspiration, lymph, and semen. Preferably, the biological fluid is blood. More preferably, the biological fluid is plasma.

One advantage of the inventive method is the ability to identify and/or characterize targets on the basis of biological, biochemical, or chemical activity, without prior knowledge of the target's molecular identity. Accordingly, the target can display a biological activity and need not undergo processing (e.g., heat-inactivation) prior to practicing the inventive method. For example, the viability of cell cultures grown on the second support material might be enhanced or diminished in the location to which an unknown target (e.g., a virus) has been transferred. Likewise, the ability of a target to affect more specific cellular functions (e.g., production of particular proteins or other cellular constituents) might be enhanced or diminished, thereby providing valuable characteristics of a target. The target also can be a live cell, which is exposed to toxic compounds once transferred to the second matrix to characterize cells resistant to toxins. Thus, the invention provides a method for the identification of novel targets or unknown targets (e.g., proteins not identified prior to practicing the inventive method) with specific biological activities. Once the unique position of the target is identified on the second support, its former position on the first support may be determined, leading to the identification of the ligand responsible for its original capture.

Ligand

For purposes of the invention, the term "ligand" as used herein refers to any biological, chemical, or biochemical entity, such as a compound, molecule, or cell that binds to a target. The ligand can be isolated from natural or synthetically produced materials. The ligand can be endogenous or exogenous to a prokaryote or eukaryote, e.g. bacteria, a fungus, yeast, plant, or a mammal. Suitable ligands for the inventive method include, but are not limited to, amino acids, peptides, nucleic acids, antibody preparations (e.g., antibody fragments, chemically-modified antibodies, and the like), carbohydrates, sugars, lipids, organic molecules, and combinations thereof, all of which can be putative therapeutic agents for the prevention or treatment of biological dysfunction.

Organic molecules include, for example, synthetic organic compounds typically employed as pharmacotherapeutic agents. Such molecules are, optionally, mass-produced by combinatorial synthetic methods or, more specifically, by strategic syntheses devised to arrive at specific molecules. Likewise, organic molecules also include natural products and analogues, whether extracted from their natural environment or strategically synthesized. The term "organic" as used herein is not intended to be limited to molecules comprised only of carbon and hydrogen, but rather is used in its broader sense as encompassing macromolecules of biological origin.

Preferably, the ligands are peptides. More preferably, the peptides consist essentially of about 1 to about 15 amino acids. The term "peptide" as used herein refers to an entity comprising at least one peptide bond, and can comprise either D and/or L amino acids. Ideally, the ligand is a peptide consisting essentially of about 2 to about 10 amino acids (e.g., about 2, 3, 4, 5, 6, 7, 8, 9, or 10 amino acids). If desired, the peptide ligands can be generated by techniques commonly employed in the generation of a combinatorial library, e.g., the split, couple, recombine method or other approaches known in the art (see, e.g., Furka et al., *Int. J Peptide Protein Res.*, 37, 487–493 (1991); Lam et al., *Nature*, 354, 82–84 (1991); International Patent Application WO 92/00091; and U.S. Pat. Nos. 5,010,175, 5,133,866, and 5,498,538). Expression of peptide libraries also is described in Devlin et al., *Science*, 249, 404–406 (1990). In peptide libraries, the number of discrete peptides of differing sequence increases dramatically with the number of coupling reactions performed, the size of the peptide, and the number of distinct amino acids utilized. For example, the random incorporation of 19 amino acids into pentapeptides produces up to 2,476,099 ($19^5$) individual peptides of differing sequence (Lam et al., supra). Combinatorial methods allow generation of libraries of ligands directly on a support. Typically, the ligands are synthesized on particles of support media such that multiple copies of a single ligand are synthesized on each particle (e.g., bead), although this is not required in the context of the invention.

The inventive method can simultaneously identify multiple ligands for a single target by providing two or more different ligands for contacting the target. Likewise, the inventive method can simultaneously characterize and/or identify multiple targets found in a single sample. In this regard, the ligand(s) or ligand-support complex(es) can be contacted with two or more targets under conditions that allow at least one target to bind to at least one ligand-support complex, thereby forming one or more target-ligand complexes (which can be further complexed to a support).

Supports and Matrices

In one embodiment of the inventive method, the ligand is attached to a support. The term "support" as used herein refers to any support matrix, such as those solid supports known in the art, which serve to immobilize the ligand. Suitable supports include, but are not limited to, membranes, filters, meshes, or particles comprised of or coated with cellulose, acrylics, polyacrylamide or polyhydroxylated methacrylate polymers, polystyrene, dextran, agarose, polysaccharides, hydrophilic vinyl polymers, polymerized derivatives of any of the foregoing, and combinations of any of the foregoing, as well as any porous or non-porous matrix to which ligands can be directly attached or on which ligands can be synthesized. Preferably, the support is inert such that chemical reaction with the target and/or the ligand is minimized. A particularly preferred support material is a polyhydroxylated methacrylate polymer. Various resins are commercially available, and, preferably, the support is a resin bead, such as a chromatographic resin bead. Many solid supports displaying potential ligands are commercially available. Alternatively, the one or more ligands of the inventive method can be indirectly attached or directly immobilized on the first support using standard methods (see, for example, Harlow and Lane, *Antibodies*, Cold Spring Harbor Laboratory, Cold Spring Harbor, N.Y. (1988); Biancala et al., *Letters in Peptide Science*, 7(291), 297 (2000); MacBeath et al., *Science*, 289, 1760–1763 (2000); Cass et al., ed., *Proceedings of the Thirteenth American Peptide Symposium. Leiden*, Escom, 975–979 (1994); U.S. Pat. No. 5,576,220; Cook et al., *Tetrahedron Letters*; 35, 6777–6780 (1994); and Fodor et al., *Science*, 251(4995), 767–773 (1991)). In one embodiment, the ligand(s) are synthesized on the surface of the support, which is advantageous in generating peptide libraries. The ligand(s) can be chemically conjugated to the support or can be attached via linkers, such as streptavidin, beta alanine, glycine, polymers containing glycine-serine, short chain hydrocarbons of the formula—$(CH_2)$—, polyethylene glycol, epsilon amino caproic acid, and linkers comprising —$O(CH_2)n$, wherein n is 1–30. If desired, the ligand(s) can be attached by one or by several different cleavable linkers, e.g., photolabile or acid labile moieties, enabling the selective detachment of a population of ligands for analysis. Detached ligands can be used, for example, as affinity purification media for proteins and enantiomeric separation (e.g., to concentrate, isolate, detect, characterize, quantify, or identify targets in a sample), as diagnostic therapeutic tools, catalysts and enhancers of chemical reactions, and as selective stabilizers of proteins.

In the inventive method, the ligand-support complexes, the target-ligand-support complexes, or the ligand(s) (depending on the parameters of the inventive method determined by the practitioner) are immobilized in a first matrix. A matrix is any solid material having at least two dimensions on which or within which a ligand-support complex, target-ligand-support complex, or ligand can be immobilized. The matrix material is selected such that the target can be transferred from the first matrix to a second matrix. Ideally, the first matrix comprises a material that is chemically inert with respect to the target and ligand. The first matrix can comprise, for example, agarose, polyacrylamide, dextran, cellulose, polysaccharide, derivatives of any of the foregoing, or combinations of any of the foregoing. Alternatively, the first matrix can comprise, for example, nylon, cotton, polyvinyldifluoride nylon, silicon, glass, styrene, polystyrene, polyacrylate, polymethacrylate, derivatives of any of the foregoing, or combinations of any of the foregoing. The matrix can be prepared as a gel, membrane, or other suitable surface.

In the context of the inventive method, at least a portion of the targets (i.e., one or more target molecules) bound to one or more ligands is transferred to a second matrix. The second matrix can be any solid material having at least two dimensions to which a target can be transferred from the first matrix. A second matrix, like the first matrix, desirably comprises a chemically inert material with respect to the target and ligand. The second matrix can be composed as the same materials suitable for use as a first matrix Preferably, the second matrix is comprised of, for example, nitrocellulose, silicon, styrene, glass, and/or polyvinyldifluoride nylon.

To transfer at least a portion of the targets of the target-ligand-support complexes to a second matrix, the first matrix can be contacted with a solution (e.g., a "transfer solution") that promotes dissociation of the target and ligand. The transfer solution can be selected from buffers of various salt concentrations, pH, or denaturation capability, organic solvents, and deionized water. Alternatively or in addition, an electric gradient can dissociate the target from the target-ligand-support complex. Transfer solutions also can comprise ligands (different from the ligand of the target-ligand-support complex), cofactors for the target, enantiomeric specific molecules, and the like. Use of different transfer solutions allow investigation of elution conditions or transfer a specific target sub-population to the second matrix.

The dissociation and transfer conditions employed in the inventive method are selected to minimize disruption of the ligand in the first matrix. In other words, the elution and transfer conditions should not release the ligand (or ligand-support complex) from the first matrix (unless this is desired). Furthermore, the target is immobilized to the second matrix such that the location of the target on the second matrix corresponds to the position of the ligand in the first matrix. Thus, once a target is selected on the second matrix, the corresponding ligand is easily determined via its position on the first matrix.

Detection/Characterization of the Target and/or Ligand

The inventive method further comprises detecting the target on the second matrix, whereupon the target that binds the ligand is characterized. The term "characterization" and words related thereto as used herein refer to the identification of any distinctive quality or trait of a target, and do not require that the precise chemical identity, e.g., the molecular formula, chemical structure, nucleotide sequence or amino acid sequence, of the target is elucidated. Indeed, characterization of the target primarily depends how the target on the second matrix is detected. In this respect, the detection method employs a molecular or biological entity that interacts with a target in some discernable way, thereby identifying the presence of a target on the second support. Many of such methods and materials are known in the art.

The target can be directly detected using, for example, immunological and radiological assays. For peptide targets, radioactive amino acid isotopes can be incorporated into the target allowing detection by exposing the second matrix to autoradiography film. Similar methods are available for other chemical targets.

Alternatively, the target can be detected by testing for a property or activity of the target, such as biological property, a chemical property, a physical property, a biochemical property, or a property that is a combination of any of the foregoing. Any biological or chemical property can be assayed that results in a detectable biological or chemical reaction, such as the enzymatic modification of a substrate. One advantage of the invention is that the target is transferred to the second matrix under conditions that retain a target's biological activity. A chemical property, e.g., a property directly related to the chemical composition of the target, can be employed. In other words, the target can be identified by the presence of specific chemical subunits or moieties or chemical structures. Physical properties useful in detection methods include, for example, spectral signal and molecular weight, which can be determined via fluorescence or mass-spectrometry, respectively. The means of detection need not detect the target alone, but can selectively identify target complexes, e.g., a target complexed with other biological entities such as co-factors or enzymes.

Detecting the target on the second matrix can comprise performing a binding assay. A binding assay typically involves contacting the second matrix with a moiety known to bind to a substrate. Binding moieties for use in binding assays include, for instance, antibodies or antigen-binding fragments thereof, proteins, or oligonucleotides. Preferably, the second matrix is contacted with an antibody or an antigen-binding fragment thereof that binds the target (or chemical or biological byproduct of the target or a fragment of any of the foregoing, if appropriate). The binding moiety preferably is labeled with a detectable tag such as, for instance, a radioisotope, a chromophore, or a fluorescent tag. In such a binding assay, a signal emitted by the detectable tag is detected, thereby signaling the presence of the target. Once the location of the target on the second matrix is elucidated, the corresponding ligand on the first matrix can be identified. Binding assays for detection of a target are further described in, for instance, Harlow and Lane, supra; Sambrook et al., *Molecular Cloning, A Laboratory Manual*, 2d edition, Cold Spring Harbor Press, Cold Spring Harbor, N.Y. (1989); Haugland, *Handbook of Fluorescent Probes and Research Chemicals* (9th ed.), Molecular Probes, Eugene, OR (2002); and Coico et al., *Current Protocols in Immunology*, v1–4, Wiley & Sons, Inc., New York, N.Y. Optionally, the inventive method can further comprise a washing step to remove excess, unbound binding moieties or markers prior to detection.

Alternatively, the inventive method can comprise performing an enzyme activity assay to characterize a target on the basis of biological activity. An enzyme substrate is applied to the second matrix under conditions which allow for enzymatic modification of the substrate by the target to form a product. The product is then detected on the second matrix, thereby identifying the location of the target. Enzyme activity assays are further described in, for example, Haugland, supra.

A cell-based assay can be performed wherein the second matrix is contacted with cells on which the target exerts some observable biologic effect such as, for example, alteration of cell growth, alternation of cell migration, cell death, production of detectable byproducts, and the like. Purely by way of illustration, the preferred target can be an antibacterial agent. The ligand of the inventive method binds potential active sites of the antibacterial agent, thereby separating the antibacterial target from a sample (e.g., a library of potential therapeutics). The antibacterial target is transferred to a second matrix, onto which a lawn of bacteria is applied. The antibacterial target is detected on the second matrix by zones of bactericidal activity. Accordingly, in addition to identifying an antibacterial target, the inventive method further allows identification of characteristics of the active site of the antibacterial target.

The detection of multiple targets or a single target with a variety of characteristics can be achieved following a single transfer of targets to the second matrix followed by multiple independent detection procedures. Accordingly, the inventive method can further comprise (vi) repeating step (v), but testing for a property that is different from the property tested in step (v). A different property of the target or a different target can be so identified. For example, if step (v) comprises an enzyme activity assay, wherein the enzyme is a dehydrogenase, the method can further comprise performing a binding assay to further characterize the target. Alternatively or in addition, the inventive method can further comprise performing a second enzyme activity assay, wherein a different activity is assayed.

In addition to characterizing a target, the ligand that binds the target can be identified. In this embodiment, the inventive method further comprises identifying the position of the detected target on the second matrix, identifying the position of the ligand or ligand-support complex in the first matrix corresponding to the position of the detected target in the second matrix, and determining the chemical identity of the ligand. If the ligand is complexed with a support in the first matrix, the ligand can be dissociated from the ligand-support complex to facilitate further characterization. The ligand also can be transferred to a third matrix (so that the support remains in the first matrix, if desired), wherein the position of the ligand within the third matrix corresponds to the position of the ligand in the first matrix. The ligand can then be detected on the third matrix using any suitable methods, such as the methods described herein. The chemical identity of the ligand desirably is determined using, for example, mass spectrometry, Edman degradation, nucleic acid sequencing, high performance liquid chromatography (HPLC), or a combination of any of the foregoing.

The second matrix can be aligned with the first matrix to identify ligand-support complexes corresponding to a detected target using any available means. For example, control beads or ligands can be present within a first matrix array to provide a point of reference for proper alignment. To this end, a population of tagged or otherwise identifiable ligands or supports (e.g., ligands or supports which bind a detectable marker) is prepared as control particles. A small number of controls are included with the target-ligand-support-complex(es) and are subsequently immobilized in the first matrix. Detection methods are employed for both the target and control entities. Signals generated by detection of the location of the control are aligned with the tagged control ligands or supports, thus orienting the immobilized supports with the second matrix. Additional or alternative methods of alignment can be employed. The orientation of the first matrix array and the orientation of the second matrix can be correlated by physical means such as discrete complementary markings aligning the first and second matrices or by aligning the matrices by complementary physical features, such as jigsaw fittings and the like.

According to one embodiment of the invention, a library of ligands is immobilized on a support and the ligand-support complexes are affixed in an array within a porous first matrix, such as an agarose gel. A sample (e.g., a solution) containing a target is brought into contact with the library of ligand-support complexes. The target-containing solution percolates through the porous first matrix to effect contact between ligand-support complex and target. Alternatively, the target-containing solution is contacted with the ligand-support complexes prior to immobilization of the ligand-support complexes in the porous first matrix. A fraction of the ligands will specifically bind target. It is generally preferred that an identified ligand will demonstrate affinity exclusively for a single target to the exclusion of other close chemical and/or structural analogues, although this is not required.

The target is dissociated from the target-ligand-support complexes through capillary action of transfer solution moving through the porous first matrix, past the target-ligand-support complexes, and carrying the eluted target from the porous first matrix where it is captured by the second matrix. Once transferred to the second matrix (e.g., a membrane), the target can be identified, detected, and located on the second matrix. By detecting the target on the second matrix and correlating the location of the target on the second matrix with the location in the first matrix array of the ligand-support complexes, it is possible to identify ligand-support complex(es) having affinity for the target.

Target-ligand complexes can be repeatedly probed in the context of the inventive method. For example, a portion of ligand on each support is linked to the support by a cleavable linker, e.g., an acid-cleavable linker a photolabile linker cleaved by focusing a laser on an individual support. Thus, when the ligand-support complex is identified, cleavage of the linker will release a percentage of ligands from the support and into the porous first matrix. The ligand can then be isolated and characterized.

Once ligands have been identified as having specificity for particular targets, those ligands can be utilized to capture, isolate, detect, and/or characterize targets using, for example, chromatographic separation. To this end, the inventive method further comprises providing multiple copies of the identified ligand and attaching each copy of the identified ligand to a support, thereby obtaining multiple ligand-support complexes. The multiple-ligand support complexes are allowed to contact a composition containing multiple copies of the target under conditions that allow the ligand to bind to the target to form multiple target-ligand-support complexes. The targets are dissociated from the target-ligand-support complexes and, if desired, subjected to additional rounds of screening. For instance, the method can further comprise performing mass spectrometry of the isolated and purified target to identify or further characterize the target. Identified ligands also can be used in diagnostic assays, to immobilize or selectively transfer targets, and as pseudo- or synthetic receptors (see, e.g., Still, *Acc. Chem. Res.*, 29, 155–163 (1996)). Additionally, the ligands themselves can be used as therapeutic agents, catalysts, and the like.

Other Considerations

The invention provides a method for detecting targets using ligands, identifying a ligand(s) that bind a target, and characterizing unknown ligands and novel targets from a sample (potentially comprising both unknown ligands and known or novel targets) based on the biological, biochemical, or chemical activity of a target. The invention also provides methods for optimizing the screening of biological and chemical entities The inventive method can be employed to determine preferred conditions under which a target (or any molecule) is transferred to the second matrix (or any matrix). For instance, the inventive method can comprise (vi) repeating step (iv) with a matrix and under conditions that are different from the previous repetitions of step (iv). In this respect, the transfer solution used to transfer the target to the second matrix can be changed to alter salt concentrations, pH, denaturant content, specific competitor molecules, and the like. The elution is then repeated under different conditions to generate a set of matrices, each having a different amount or different population of target. The method further comprises (vii) detecting the targets on each of the matrices of step (vi), and (viii) comparing the amount of the target on the second matrix and each of the matrices of step (vi). This embodiment of the inventive method also can be employed to determine the preferred conditions under which the ligand dissociates from the target, possible elution conditions for bulk affinity purification, or to prioritize various ligands and gain insight into their binding characteristics.

In addition, the inventive method provides a means to study the binding characteristics of a target and/or ligand. For example, step (iv) of the method can be carried out in a medium containing a competitive binding agent, which binds to the target of at least one target-ligand-support complex or target-ligand complex, thereby causing the target to dissociate from the ligand-support complex or ligand within the first matrix. By "competitive binding agent" is meant any biological or chemical entity that binds to the target and is not the ligand. Preferably, the competitive binding agent is selected from the group consisting of *Bacillus anthracis, Brucella melitensis,* Ebola Zaire virus, Botulinum neurotoxin, Staphylococcus enterotoxin B, and West Nile virus. The competitive binding agent also can be portion or fragment of any of the forgoing. Likewise, the competitive binding agent can be selected from the group consisting of ricin, sulfur mustard, soman, sarin, tabun, VX, and phosgene, or can comprise a fragment of any of the foregoing. Addition of a competitive binding agent to the first matrix enables characterization of the interaction between the ligand and the target (e.g., binding affinity or specificity). Competitive elution of the target in the presence of potential substrates also allows identification of active site antagonists and agonists.

The inventive method also finds utility in separation of structural isoforms and enantiomers from a sample. For example, separation of conformationally distinct forms of a target can be achieved by transferring the target to the second matrix under conditions that allow elution of only one form of the target. Additionally, detection methods that are specific to one isoform of a target can be employed. Ligands that bind different forms of a target can then be identified. Such ligands can separate isoforms in a wide variety of scenarios, including removal of misfolded or post-translationally modified proteins, identification of mutated targets, and the like.

In addition, complexed forms of a target in a sample can be identified, separated, or quantified by employing transfer conditions or detection systems favoring complexed proteins. Likewise, the second matrices can be sequentially probed for one member of a complex and re-probed for a second member of a complex. If desired, a ligand that binds multiple members of a complex can be identified, which are useful purifying protein complexes from a sample. The inventive method also can be used for quantifying the amount of target in a sample, detecting differences in proteins expressed from cells under different conditions, or in separating and detecting proteins present in biological samples (e.g., plasma or other biological fluid) associated with a disease state versus a normal state.

The following examples further illustrate the invention but, of course, should not be construed as in any way limiting its scope.

EXAMPLES

Example 1

This example illustrates a preferred embodiment of the inventive method.

A library of peptide ligands is synthesized or immobilized on beads of chromatography resin to create a combinatorial bead library (a library of ligand-support complexes). The resin beads then are contacted with a target-containing mixture (i.e., a sample), and immobilized in a porous gel matrix (i.e., a first matrix) as follows. The gel system is composed of layers. A 1% agarose gel base is poured onto a tray and represents part of a "first matrix." The agarose gel base serves to provide stability and robustness to the gel system so that it can be manipulated and handled repeatedly. After the first matrix has solidified but not reached room temperature, a volume of 0.5% low-melting temperature (LMT) agarose sufficient to cover the top of the agarose gel base with the combinatorial bead library in a monolayer (generally one-tenth the volume used in the base) is mixed with a volume of the combinatorial bead library that is sufficient to substantially cover the surface of the agarose gel base in a well-separated monolayer (one tenth of the volume of 0.5% LMT agarose in this instance). The target-ligand-support complexes are added to the LMT agarose at a temperature of approximately 40° C. The mixture is vortexed momentarily and poured immediately onto the agarose base layer. The target-ligand-support complex-containing layer is spread over the surface of the agarose gel base. This results in a monolayer of target-ligand-support complexes immobilized on the agarose gel base in a two-dimensional array, with the beads covered with an extremely thin layer of LMT agarose. The gel system is held at 4° C. until solidification.

The gel system is placed on absorbent paper, typically 3MM paper, that is suspended over a tank of transfer buffer. The absorbent paper is positioned such that transfer buffer is wicked up through the paper. The gel system is placed with the target-ligand-support complexes facing upward. A support (i.e., second matrix) that will bind proteins, typically a nitrocellulose or polyvinylidene difluoride (PVDF) membrane is placed on top the gel. Any air bubbles between the gel system and second matrix are removed by rolling a pipette over the membrane and gel system. Two layers of absorbent paper are placed on top the membrane, followed by several layers of paper towels. A weight sufficient to ensure tight apposition of gel, membrane, and paper is placed on top. The transfer is allowed to proceed for a time period sufficient to transfer an adequate amount of target protein from the beads to the membrane. The result of this setup is the uniform capillary transfer of buffer from the tank, through the entire gel system and membrane, and into the absorbent paper on top. This process carries the target proteins from the beads to the membrane. The signal generated by a detection system, e.g., a chemiluminescent signal captured on x-ray film, is aligned with the first support so that beads bearing ligands that bound the target can be unambiguously identified.

The composition of the transfer buffer can be tailored to conditions that are most appropriate for a desired use. In one example fibrinogen was eluted from target-ligand-support complexes under increasingly stringent conditions. Certain target-ligand-support complexes generated signals under the different conditions, demonstrating that affinities of target protein to ligands can be determined using different transfer buffers. It is possible to transfer target protein to a second matrix using elution conditions under which the activity of the target protein is preserved. Target protein can be transferred to a second matrix using different buffers serially or in parallel.

Once the target proteins have been captured on the second matrix the identity of individual proteins can be determined via a number of techniques. Typical detection methods involve antibody techniques, such as those employed in Western Blots, although radiolabeled probes and enzyme activity can be used as a detection assay.

Example 2

This example illustrates the use of the inventive method to identify ligands that bind purified osteoprotegrin, which can be used a resin in affinity chromatography.

A library of ligand-support complexes (polymethacrylate beads bearing hexameric peptide ligands in which the amino acid at the amino terminal position was a known, D-isoform; 5 mg) was incubated with 200 µl of 1% casein, 3% bovine serum albumin for two hours at 22° C. to block non-specific binding sites. Osteoprotegrin ligand protein (OPGL, 3 µl of 330 µg/ml) was added to the blocking buffer, and the beads were incubated while rocking for 15 hours at 4° C. Separate reactions were performed using ligand-support complex sub-libraries in which the amino-terminal amino acid of the peptide ligand was one of 16 natural amino acids (excluding cysteine, glutamine, and methionine). Following incubation, the sub-libraries were separately washed with 50 ml of 20 mM Tris, 500 mM NaCl, 0.1% Tween-20 (TTBS), pH 7.2, to remove non-bound and weakly bound target protein. Approximately 1 mg of each sub-library was mixed with 50 µl of 0.5% low melting point agarose (LMP). The LMP agarose-bead mixture was spotted on top of a pre-formed 1% agarose base (10 ml) to for a gel system. The LMP agarose-bead mixture was allowed to harden at 4° C. for about 15 min. Following solidification, the gel system was placed on a piece of filter paper pre-wetted with transfer buffer (4 M Guanidinium HCl (GuHCl), pH 5), the ends of which were submerged in a tank filled with transfer buffer.

A piece of nitrocellulose membrane (i.e., a second matrix), pre-wetted with transfer buffer and cut to the size of the gel system, was laid atop the gel system. Two pieces of pre-wetted filter paper were placed atop the membrane, and several pieces of dry paper towel were placed atop the filter paper. A 300 g weight was placed on top of the apparatus, and the transfer proceeded for 18 hr at 22° C.

Following the transfer of proteins to the membrane, the membrane was separated from the gel, rinsed with TTBS buffer, and the non-specific binding sites blocked by incubation of the membrane with 5% non-fat milk for 2 hours at room temperature. The target protein was detected using polyclonal rabbit anti-mouse OPGL antibody. The membrane was washed with TTBS, and the binding of the primary antibody was detected with goat anti-rabbit HRP-labeled secondary antibody. The target protein was detected using an enhanced chemiluminescent substrate that generated spots on autoradiography film where the bound protein was located on the membrane. The film was aligned with the original gel, and beads that aligned with spots on the film were picked from the gel with a curved needle. The beads were warmed to 70° C. to melt off contaminating agarose, and washed with 8 M Guanidinium HCl, methanol and water. The beads were re-exposed to OPGL protein as described above, re-transferred, and aligned. Those beads that aligned a second time were picked, washed, and the ligands sequenced on an ABI sequencer. The following sequences were obtained from a total of tens of thousands of ligands (all of which have a D amino acid in the N-terminal position and an Ala in the C-terminal position): LVTVWPA (SEQ ID NO:1), YDYHELA (SEQ ID NO:2), LHHPPIA (SEQ ID NO:3), RANKTQA (SEQ ID NO:4), and TTPSKKA (SEQ ID NO:5).

This example demonstrates the use of inventive method to identify ligands for a predetermined target protein followed by the elucidation of the amino acid sequences of the ligands.

Example 3

This example illustrates the detection of a target protein via its biological activity. Biological activity can be used to detect the presence and activity of novel proteins in conditions under which the identity of neither the protein nor its cognate ligand is known. To perform assays based on biological, biochemical, or enzymatic activity, the target protein must be transferred to the second matrix, in this instance a membrane, under conditions which maintain activity.

BChE (2 mg/ml) was immobilized on procainimide (PAM) ligand bound to chromatography resin beads to form target-ligand-support complexes. The chromatography resin beads were then immobilized in 0.5% LMP agarose poured on top of a 1% regular agarose gel base to form a gel system, as described above. The LMP agarose-bead mixture was allowed to harden at 4° C. for 15 minutes. Following solidification, the gel system was placed on a piece of filter paper pre-wetted with transfer buffer (0.5M phosphate buffer/0.5M NaCl, pH 7.2), the ends of which were submerged in a tank filled with transfer buffer. A piece of nitrocellulose membrane, pre-wetted with transfer buffer and cut to the size of the gel, was laid atop the gel system. Two pieces of pre-wetted filter paper were placed atop the membrane, and several pieces of dry paper towel were placed on top. A 100 g weight was placed atop the apparatus, and the apparatus was left overnight at 22° C.

Following transfer of the protein, the nitrocellulose membrane was separated from the gel system. A second piece of nitrocellulose membrane was soaked in transfer buffer to serve as a negative control. Cholinesterase substrate solution (BTC=5 mmol/l butyrylthiocholine iodide, 0.25 mmole/l 5,5'-Dithiobis-2-Nitrobenzoic acid, pH 7.2) was pipetted onto the membranes and the gel system to detect untransferred protein. The membranes and gel system were incubated in the dark at 22° C. for one hour. Yellow color developed on the membrane onto which the target protein was transferred. No yellow color was observed on the control membrane. Some residual target protein remained on the resin beads in the gel system, indicating that not all of the target protein had transferred under these conditions.

This example demonstrates that target protein can be detected and characterized on a second matrix by testing for-biological activity. In particular, the presence of yellow color on the transfer membrane indicates that BCHE was transferred from the resin beads in the gel system, captured on the membrane, and remained active.

Example 4

This example illustrates use of the inventive method to identify conditions underwhich proteins elute from ligands. Understanding elution characteristics is instrumental to the development of affinity purification processes for bulk purification of targets from complex mixtures. Of the multiple potential ligands that bind a particular target, ligands that bind and elute under preferential conditions can be detected by testing multiple elution conditions serially or in parallel. In this example, fibrinogen was eluted from library of ligand-support complexes under several conditions. Different ligands were found to elute the protein under different conditions.

A library of ligand-support complexes (resin beads, 32 mg) bearing 6-amino acid ligands synthesized on 650-M amino ToyoPearl resin (Tosohaas BioScience) with Ala-epsilon amino caproic acid (EACA) spacer were washed with 20% methanol and swollen for 1 hr in 20 mM citrate buffer. The resin beads were blocked with 1% (w/v) casein/3% (w/v) bovine serum albumin for 1 hr at 22° C. The resin beads were incubated with 3.2 ml human platelet-poor plasma for 1 hr at 22° C., and washed with 50 ml 150 mM NaCl, 20 mM citrate, pH 7.12. A portion of the library (320 µg) was mixed with 240 µl 0.5% low melting point (LMP) agarose, which was subsequently spread over 30 ml of a 1% agarose base (i.e., a first matrix). The transfer of target protein to a second matrix was performed as described in Examples 1–3 onto PVDF membrane. The initial transfer buffer comprised 0.45 M NaCl/20 mM citrate, pH 7.2, and contacted the gel system and PVDF membrane for 24 hours. Following the initial transfer, the gel system was removed from the apparatus and a second and third round of target transfer was performed. A new membrane was placed atop the gel system and exposed to transfer buffer (1.0 M NaCl (second transfer) or 1.5 M NaCl (third transfer)/20 mM citrate, pH 7.12) for 24 hours. Following the third transfer procedure, a final transfer procedure was performed wherein the gel system and a new membrane were exposed 6 M GuHClI for eight hours. The membranes were stored moist at 4° C. until completion of all of the transfer procedures, at which time all membranes were processed simultaneously.

Each membrane was blocked with 5% non-fat milk for two hours at 22° C. The membranes were then incubated with polyclonal sheep anti-human fibrinogen antibody (Affinity Biologicals) diluted 1:8000 for 1 hour at 22° C. The membranes were washed with TTBS, and transfer protein was detected following incubation with a second HRP-conjugated sheep anti-human fibrinogen antibody diluted 1:8000 for 1 hour at 22° C. Signals from the target protein-bound antibody were detected with an enhanced chemiluminescent horseradish peroxidase (HRP) substrate (incubated for 10 minutes) and captured on X-ray film. The films were aligned with the gel system, and the corresponding ligand-resin beads were picked from the gel system. The resin beads were washed, and the attached ligands were sequenced. The following sequences was obtained from the screened resin: IAIWVA (SEQ ID NO: 13). The following other amino acid sequences also were identified: AREADVA (SEQ ID NO:6); YEYARP (SEQ ID NO:7); WDGATY (SEQ ID NO:8); FDPHWS (SEQ ID NO:9); FSDVED (SEQ ID NO: 10); FEYAPS (SEQ ID NO:11); and HGTWEP (SEQ ID NO:12).

This example demonstrates the use of the inventive method to identify ligands for a predetermined target protein. Different ligands were found to elute the protein under different conditions, which provides valuable information for using the identified ligands in affinity chromatography protocols.

Example 5

This example illustrates a method for identifying ligands that bind protein agents associated with disease, namely prion proteins that are associated with transmissible spongiform encephalopathies.

A library of 650-M amino polymethacrylate resin beads bearing ligands that were two amino acids long (5 mg) was blocked with 1% (w/v) casein for 18 hours at 4° C. with rocking. Normal hamster brain homogenate diluted 1:10 with PBS was incubated with 0.5% (w/v) sarkosyl for 30 minutes. A 1:10 dilution of the treated material (1 ml) was incubated with the blocked ligand-attached resin beads for one hour at 22° C. with rocking. A portion of the target-ligand-resin bead complexes (90 µl) was mixed with 800 µl of 0.5% LMP agarose and poured over a gel base (i.e., first matrix) comprising 9 ml of 1% agarose. The LMP agarose-bead mixture was allowed to harden at 4° C. for approximately 15 minutes to form a gel system. The transfer of target protein to a second matrix, a PVDF membrane, was performed as described in Examples 1–3 using 6M Guanidinium HCL as the transfer buffer. The transfer reaction was allowed to proceed overnight. Following transfer, the PVDF membrane was separated from the gel system and blocked with 5% milk. Prion protein targets (PrPc) were detected using 3F4, an antibody specific for the denatured form of PrPc, as the primary antibody. An HRP-labeled goat anti-mouse secondary antibody was used in conjunction with an enhanced chemiluminescent substrate to detect bound PrPc on the membrane, the signal of which was captured on X-ray film. The films were aligned with the gel system, and corresponding ligand-attached resin beads retrieved and washed. The ligands were sequenced to identify the amino acid sequence.

This example demonstrates the ability of the inventive method to identify ligands that bind to proteins involved in disease. The identified ligands can be used to diagnose the presence of the target in various complex mixtures (e.g., biological samples) or to remove disease-causing target proteins from mixtures.

Example 6

This example illustrates the identification of multiple targets by performing a single incubation of a library of ligand-support complexes with a sample in conjunction with multiple detection steps.

The following resins were used: a resin comprising fibrinogen-binding ligands (GPRPGG (SEQ ID NO: 23)) was synthesized directly on 650-M amino ToyoPearl resin (Tosohaas Bioscience), an alpha-1 protease inhibitor (API)-binding resin comprised of green agarose PIKSIT® beads (a control for API-binding), and a ligand-support complex resin consisted of a library of 650-M amino resins (Tosohaas BioScience) bearing hexamer ligands comprising a D-amino acid in the N-terminal position. The GPRPGG (SEQ ID NO: 23) resin (2.5 mg, pre-swollen) and hexamer library resin (2 mg, pre-swollen) were blocked with 1% (w/v) casein/3% (w/v) bovine serum albumin (BSA) for 3 hours at 22° C. in separate tubes, afterwhich the blocking buffer was drained. Human platelet-poor plasma (20 ml) was added to the GPRPGG (SEQ ID NO: 23) resin and hexamer library resin and allowed to bind for 18 hours at 4° C. with rocking. The resins were washed with 50 ml TTBS, leaving 50 µl TTBS in the tube post-wash. A portion of each washed resin (5 µl) and 2.5 mg of green agarose PIKSIT® beads, pre-incubated with pure API, were mixed separately with 330 ml 0.5% LMP agarose. Each of the three resin mixtures was spotted onto a 1% agarose base such that the GPRPGG (SEQ ID NO: 23) resin, the hexamer library resin, and the green agarose PIKSIT® resin were located on non-overlapping areas of the gel base. The target proteins were transferred by serial elution onto different nitrocellulose membranes under the following conditions: 0.2 M NaCl/20 mM citrate, pH 7.12, for eight hours, 1.5 M NaCl/20 mM citrate, pH 7.2, for 15 hours, 2 M NaCl/20 mM citrate, pH 7.2, for eight hours, and 4M GuHCl, pH 5, for 13 hours. Membranes were stored at 4° C. until processing.

All membranes were processed simultaneously. The membranes were first blocked in 5% non-fat milk for two hours at 22° C. Sheep anti-human fibrinogen polyclonal antibody was used as a primary antibody to detect fibrinogen target proteins. After a subsequent washing step, the membranes were probed with HRP-conjugated sheep anti-human fibrinogen antibody, which binds the primary antibody. The signal was developed on autoradiography film with an enhanced chemiluminscent substrate for HRP.

Following fibrinogen detection, the membranes were stripped of bound antibody by incubation with TTBS at 50° C. The membranes were re-blocked and exposed to goat anti-human alpha-1 antitrypsin polyclonal antibody. After a subsequent washing step, the membranes were probed with HRP-conjugated rabbit anti-goat IgG polyclonal antibody, and the resulting signal was detected with enhanced chemiluminescent HRP substrate and captured on X-ray film.

In this example, ligands known to bind to different plasma proteins were exposed to a plasma sample comprising target proteins. The employed detection methods demonstrated that both fibrinogen and API were simultaneously transferred to the membranes from the gel system. In addition, only one of the two proteins was bound to each resin bead. Accordingly, this example demonstrates that multiple proteins on a membrane detected with subsequent stripping and re-probing.

Example 7

This example illustrates use of the inventive method to identify ligands that preferentially bind a target protein, API, in a biological fluid sample.

A library of ligand-support complexes was obtained by generating a library of peptide hexamers comprising a D-amino acid on the N-termius on ToyoPearl 650-M amino resin (Tosoh BioScience). Approximately 10 mg of the library of ligand-support complexes was washed, swollen, washed, and incubated with 1 ml plasma diluted with an equal volume of equilibration buffer (EQ Buffer; 140 mM NaCl, 20 mM Citrate, pH 7.4) in a BioRad column for 1 hour at room temperature with tumbling agitation. The BioRad column was drained, and the resin beads washed with 10 column volumes of EQ Buffer. The resin beads (now target-ligand-support complexes) were resuspended in 1 ml EQ Buffer. Approximately 10 µl of the resin beads were mixed with 900 µl of LMP agarose as described in Examples 1–3. The resin-agarose mixture was spread on the surface of a solidified, normal agarose base (a first matrix) to form a gel system. The resin-agarose mixture was allowed to solidify at 4° C. A transfer system using a membrane as the second matrix was prepared as described in Examples 1–3. Transfer of plasma proteins to the second matrix membrane occurred overnight at room temperature using EQ Buffer+2 M NaCl. The membrane was processed using an HRP-conjugated polyclonal goat anti-human alpha-1 antitrypsin antibody (ICN), which binds alpha-1 antitrypsin (API). Location of API protein on the membrane was determined. Resin beads in the gel system that aligned with locations of API protein on the membrane were selected, washed, and re-incubated with plasma. Plasma protein transfer from the target-ligand-support complexes to a membrane and detection of API target protein was repeated to confirm potential positives and unambiguously identify ligand-resin bead complexes that bound target protein. The positive resin beads were collected, cleaned, and the attached ligands were sequenced by Edman degradation on an ABI sequencer. Several sequences were identified and synthesized for use as preparative scale resins to purify API from plasma that had been depleted of fibrinogen and Apo-A1 lipoprotein. The following sequences were among those identified: KFQARA (SEQ ID NO:14); KWSITN (SEQ ID NO:15); KSPRWP (SEQ ID NO:16); and AKVSKG (SEQ ID NO:17). The identified ligands were shown to preferentially bind to API.

Ligands specific for a target protein can be identified from a peptide library using the inventive method, as demonstrated by this example. The identified ligands preferentially captured a pre-determined target protein, and are appropriate for large-scale target protein purification.

Example 8

This example illustrates the identification of ligands that bind to a protein complex, namely Factor VIII (fVIII) and von Willebrand factor (vWF).

Approximately 10 mg of ligand-support complexes displaying a library of peptide hexamers was prepared as described in Example 7. Resin beads displaying the peptide library were incubated in a BioRad column with 1 ml of plasma diluted with an equal volume of EQ Buffer for one hour at room temperature with tumbling agitation. The BioRad column was drained, rinsed, and washed with 10 column volumes of EQ Buffer. Resin beads (now target-ligand-support complexes) were resuspended in 1 ml EQ Buffer. Approximately 10 µl of resin beads were then combined with 900 µl of LMP agarose and spread across an agarose base. The resin-agarose mixture was allowed to harden to form a gel system, and a target protein transfer procedure was set up as described in Examples 1–7. The target protein transfer from the target-ligand-support complexes onto a second matrix (membrane) proceeded overnight at room temperature in EQ buffer+2 M NaCl. The membrane was processed with an HRP-labeled polyclonal antihuman vWF antibody (Enzyme Research Labs) for one hour, and the location of the vWF target protein on the membrane was determined using standard ECL plus chemiluminescent substrate. Resin beads that aligned with the locations of target protein on the membrane were selected, washed, and re-incubated with plasma. Transfer of target protein to a second matrix (membrane) and detection of target protein on the membrane was repeated to confirm potential positives and unambiguously identify resin beads comprising ligands that bind vWF. The positive resin beads were collected, cleaned, and the attached ligands were sequenced by Edman degradation on an ABI sequencer. Several sequences were identified and synthesized for use in preparative scale resins. In addition, resin beads incubated with unfiltered plasma were moved to wells of a 96-well microtiter plate and incubated with Coatest fvIII activity assay kit (Chromagenix). Resin beads displaying ligands that bound fvIII as identified by a color change (yellow) were selected for fuirther evaluation. Several ligands were identified that co-purify vWF and fVIII including FSYDED (SEQ ID NO: 18), LEDnal'EE (SEQ ID NO:19), WEEPEQ (SEQ ID NO:20), EADnaLED (SEQ ID NO:21), andYVD-EDD (SEQ ID NO:22).

This example illustrates one embodiment of the inventive method wherein protein complexes are characterized using multiple detection methods and removed from a biological sample.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of determining a property of a target that binds to a ligand, which method comprises:
   (i) providing one or more ligands,
   (ii) immobilizing each of the ligands in a first matrix, wherein each of the ligands has a different position within the first matrix,
   (iii) contacting the ligands within the first matrix with one or more targets wherein at least one target binds to at least one ligand, thereby forming one or more target-ligand complexes within the first matrix,
   (iv) transferring in a transfer buffer, at least a portion of the target of at least one target-ligand complex within the first matrix to a second matrix so that the ligand of the target-ligand complex remains in the first matrix, wherein the position of the target within the second matrix identifies the position of the ligand within the first matrix, and
   (v) detecting the target on the second matrix, whereupon a property of the target that binds to a ligand is determined, wherein said property is a biological property, a chemical property, a physical property, a biochemical property or a property which is any combination thereof.

2. The method of claim 1, wherein, in step (i), two or more ligands are provided.

3. The method of claim 1, wherein, in step (iii), the ligands within the first matrix are contacted with two or more targets wherein at least one target binds to at least one ligand, thereby forming one or more target-ligand complexes within the first matrix.

4. The method of claim 1, wherein the one or more targets is in a biological fluid.

5. The method of claim 4, wherein the biological fluid is selected from the group consisting of blood, plasma, serum, a cell homogenate, a tissue homogenate, a conditioned medium, a fermentation broth, cerebrospinal fluid, urine, saliva, milk, ductal fluid, tears, perspiration, lymph, and semen.

6. The method of claim 1, wherein the target is selected from the group consisting of proteins, peptides, amino acids, nucleic acids, carbohydrates, lipids, drugs, synthetic inorganic compounds, synthetic organic compounds, isoforms of any of the foregoing, eukaryotic cells, prokaryotic cells, viruses, and combinations of any of the foregoing.

7. The method of claim 1, wherein the one or more targets are plasma proteins.

8. The method of claim 7, wherein the plasma proteins are proteins selected from the group consisting of butyryl cholinesterase, fibrinogen, α-I proteinase inhibitor, prion protein, apolipoprotein A1, immunoglobulins, paraoxonase, coagulation factors, and combinations of any of the foregoing.

9. The method of claim 1, wherein the ligands are selected from the group consisting of amino acids, peptides, nucleic acids, antibody preparations, carbohydrates, sugars, lipids, organic molecules, and combinations thereof.

10. The method of claim 9, wherein the ligands are peptides consisting essentially of about 2 to about 15 amino acids.

11. The method of claim 1, wherein the first matrix comprises a material selected from the group consisting of polysaccharide, polyhydroxylated methacrylate polymer, resin, nylon, cotton, silicon, glass, polystyrene, polyacrylate, polymethacrylate, and combinations of any of the foregoing.

12. The method of claim 1, wherein the second matrix comprises a material selected from the group consisting of nitrocellulose, silicon, styrene, and polyvinyldifluoride nylon.

13. The method of claim 11, wherein said first matrix comprises a material selected from the group consisting of polyhydroxylated methacrylate polymer and ToyoPearl resin.

14. The method of claim 11, wherein said first matrix comprises a material selected from the group consisting of dextran, cellulose, agarose, polyacrylamide, polyvinyldifluoride nylon, styrene, and combinations of any of the foregoing.

* * * * *

SEQUENCE LISTING

```
<160> NUMBER OF SEQ ID NOS: 23

<210> SEQ ID NO 1
<211> LENGTH: 7
<212> TYPE: PRT
<213> ORGANISM: Artificial
<220> FEATURE:
<223> OTHER INFORMATION: Synthetic

<400> SEQUENCE: 1

Leu Val Thr Val Trp Pro Ala
1               5

<210> SEQ ID NO 2
<211> LENGTH: 7
<212> TYPE: PRT
<213> ORGANISM: Artificial
<220> FEATURE:
<223> OTHER INFORMATION: Synthetic

<400> SEQUENCE: 2

Tyr Asp Tyr His Glu Leu Ala
1               5

<210> SEQ ID NO 3
<211> LENGTH: 7
<212> TYPE: PRT
<213> ORGANISM: Artificial
<220> FEATURE:
<223> OTHER INFORMATION: Synthetic

<400> SEQUENCE: 3

Leu His His Pro Pro Ile Ala
1               5

<210> SEQ ID NO 4
<211> LENGTH: 7
<212> TYPE: PRT
<213> ORGANISM: Artificial
<220> FEATURE:
<223> OTHER INFORMATION: Synthetic

<400> SEQUENCE: 4

Arg Ala Asn Lys Thr Gln Ala
1               5

<210> SEQ ID NO 5
<211> LENGTH: 7
<212> TYPE: PRT
<213> ORGANISM: Artificial
<220> FEATURE:
```

<223> OTHER INFORMATION: Synthetic

<400> SEQUENCE: 5

Thr Thr Pro Ser Lys Lys Ala
1               5

<210> SEQ ID NO 6
<211> LENGTH: 7
<212> TYPE: PRT
<213> ORGANISM: Artificial
<220> FEATURE:
<223> OTHER INFORMATION: Synthetic

<400> SEQUENCE: 6

Ala Arg Glu Ala Asp Val Ala
1               5

<210> SEQ ID NO 7
<211> LENGTH: 6
<212> TYPE: PRT
<213> ORGANISM: Artificial
<220> FEATURE:
<223> OTHER INFORMATION: Synthetic

<400> SEQUENCE: 7

Tyr Glu Tyr Ala Arg Pro
1               5

<210> SEQ ID NO 8
<211> LENGTH: 6
<212> TYPE: PRT
<213> ORGANISM: Artificial
<220> FEATURE:
<223> OTHER INFORMATION: Synthetic

<400> SEQUENCE: 8

Trp Asp Gly Ala Thr Tyr
1               5

<210> SEQ ID NO 9
<211> LENGTH: 6
<212> TYPE: PRT
<213> ORGANISM: Artificial
<220> FEATURE:
<223> OTHER INFORMATION: Synthetic

<400> SEQUENCE: 9

Phe Asp Pro His Trp Ser
1               5

<210> SEQ ID NO 10
<211> LENGTH: 6
<212> TYPE: PRT
<213> ORGANISM: Artificial
<220> FEATURE:
<223> OTHER INFORMATION: Synthetic

<400> SEQUENCE: 10

Phe Ser Asp Val Glu Asp
1               5

<210> SEQ ID NO 11
<211> LENGTH: 6
<212> TYPE: PRT
<213> ORGANISM: Artificial
<220> FEATURE:
<223> OTHER INFORMATION: Synthetic

```
<400> SEQUENCE: 11

Phe Glu Tyr Ala Pro Ser
1               5

<210> SEQ ID NO 12
<211> LENGTH: 6
<212> TYPE: PRT
<213> ORGANISM: Artificial
<220> FEATURE:
<223> OTHER INFORMATION: Synthetic

<400> SEQUENCE: 12

His Gly Thr Trp Glu Pro
1               5

<210> SEQ ID NO 13
<211> LENGTH: 6
<212> TYPE: PRT
<213> ORGANISM: Artificial
<220> FEATURE:
<223> OTHER INFORMATION: Synthetic

<400> SEQUENCE: 13

Ile Ala Ile Trp Val Ala
1               5

<210> SEQ ID NO 14
<211> LENGTH: 6
<212> TYPE: PRT
<213> ORGANISM: Artificial
<220> FEATURE:
<223> OTHER INFORMATION: Synthetic

<400> SEQUENCE: 14

Lys Phe Gln Ala Arg Ala
1               5

<210> SEQ ID NO 15
<211> LENGTH: 6
<212> TYPE: PRT
<213> ORGANISM: Artificial
<220> FEATURE:
<223> OTHER INFORMATION: Synthetic

<400> SEQUENCE: 15

Lys Trp Ser Ile Thr Asn
1               5

<210> SEQ ID NO 16
<211> LENGTH: 6
<212> TYPE: PRT
<213> ORGANISM: Artificial
<220> FEATURE:
<223> OTHER INFORMATION: Synthetic

<400> SEQUENCE: 16

Lys Ser Pro Arg Trp Pro
1               5

<210> SEQ ID NO 17
<211> LENGTH: 6
<212> TYPE: PRT
<213> ORGANISM: Artificial
<220> FEATURE:
<223> OTHER INFORMATION: Synthetic
```

```
<400> SEQUENCE: 17

Ala Lys Val Ser Lys Gly
1               5

<210> SEQ ID NO 18
<211> LENGTH: 6
<212> TYPE: PRT
<213> ORGANISM: Artificial
<220> FEATURE:
<223> OTHER INFORMATION: Synthetic

<400> SEQUENCE: 18

Phe Ser Tyr Asp Glu Asp
1               5

<210> SEQ ID NO 19
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is naphthylalanine

<400> SEQUENCE: 19

Leu Glu Asp Xaa Glu Glu
1               5

<210> SEQ ID NO 20
<211> LENGTH: 6
<212> TYPE: PRT
<213> ORGANISM: Artificial
<220> FEATURE:
<223> OTHER INFORMATION: Synthetic

<400> SEQUENCE: 20

Trp Glu Glu Pro Glu Gln
1               5

<210> SEQ ID NO 21
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is naphthylalanine

<400> SEQUENCE: 21

Glu Ala Asp Xaa Leu Glu Asp
1               5

<210> SEQ ID NO 22
<211> LENGTH: 6
<212> TYPE: PRT
<213> ORGANISM: Artificial
<220> FEATURE:
<223> OTHER INFORMATION: Synthetic

<400> SEQUENCE: 22

Tyr Val Asp Glu Asp Asp
1               5
```

```
-continued

<210> SEQ ID NO 23
<211> LENGTH: 6
<212> TYPE: PRT
<213> ORGANISM: Artificial
<220> FEATURE:
<223> OTHER INFORMATION: Synthetic

<400> SEQUENCE: 23

Gly Pro Arg Pro Gly Gly
1               5
```